United States Patent [19]

Seidy

[11] Patent Number: 4,862,574
[45] Date of Patent: Sep. 5, 1989

[54] PANTY PROTECTOR

[75] Inventor: Wassim Seidy, Somerset, N.J.

[73] Assignee: Personal Products Company, Milltown, N.J.

[21] Appl. No.: 313,102

[22] Filed: Feb. 21, 1989

Related U.S. Application Data

[63] Continuation of Ser. No. 018,259, Feb. 24, 1987.

[51] Int. Cl.⁴ ............................................. B23P 17/00
[52] U.S. Cl. .................................... 29/415; 29/527.2; 604/385.1; 604/398; 156/252; 156/299
[58] Field of Search ...................... 604/385.1, 387, 389, 604/390, 398; 156/250, 252, 253, 269, 256, 263, 265, 289, 299, 300, 301, 291; 29/415, 527.2

[56] References Cited

U.S. PATENT DOCUMENTS

| | | | |
|---|---|---|---|
| 3,192,927 | 7/1965 | Chauviere | 604/385.1 |
| 4,285,343 | 8/1981 | McNair | 604/385.1 |
| 4,409,049 | 10/1983 | Passafiume et al. | 156/291 |
| 4,589,876 | 5/1986 | Van Tilburg | 604/385.1 |

Primary Examiner—Noah P. Kamen
Attorney, Agent, or Firm—Andrea L. Colby; A. A. Ciamporcero, Jr.

[57] ABSTRACT

Improvements are made in a panty protector of the kind comprising adhesive attachment and provided with transversely extending flaps. The peripheral shape of the protector is such that it is possible to produce the sheet of material of construction for the protector and simply cut said shapes out of said sheets with minimal waste.

1 Claim, 4 Drawing Sheets

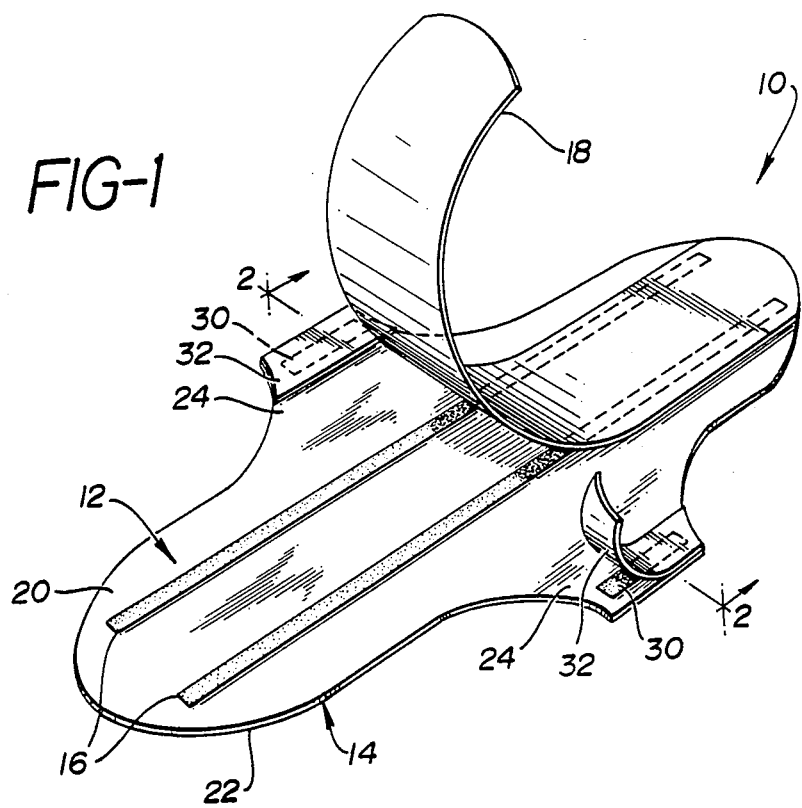
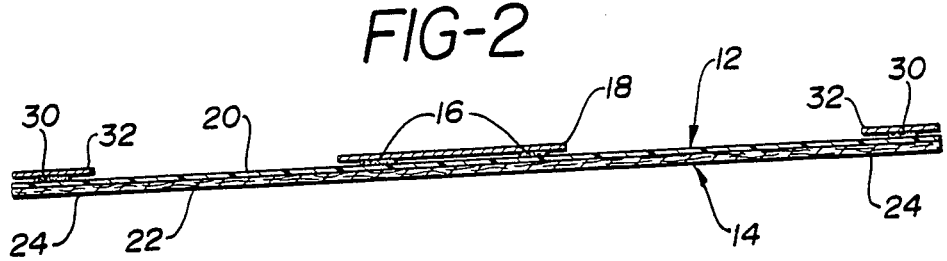

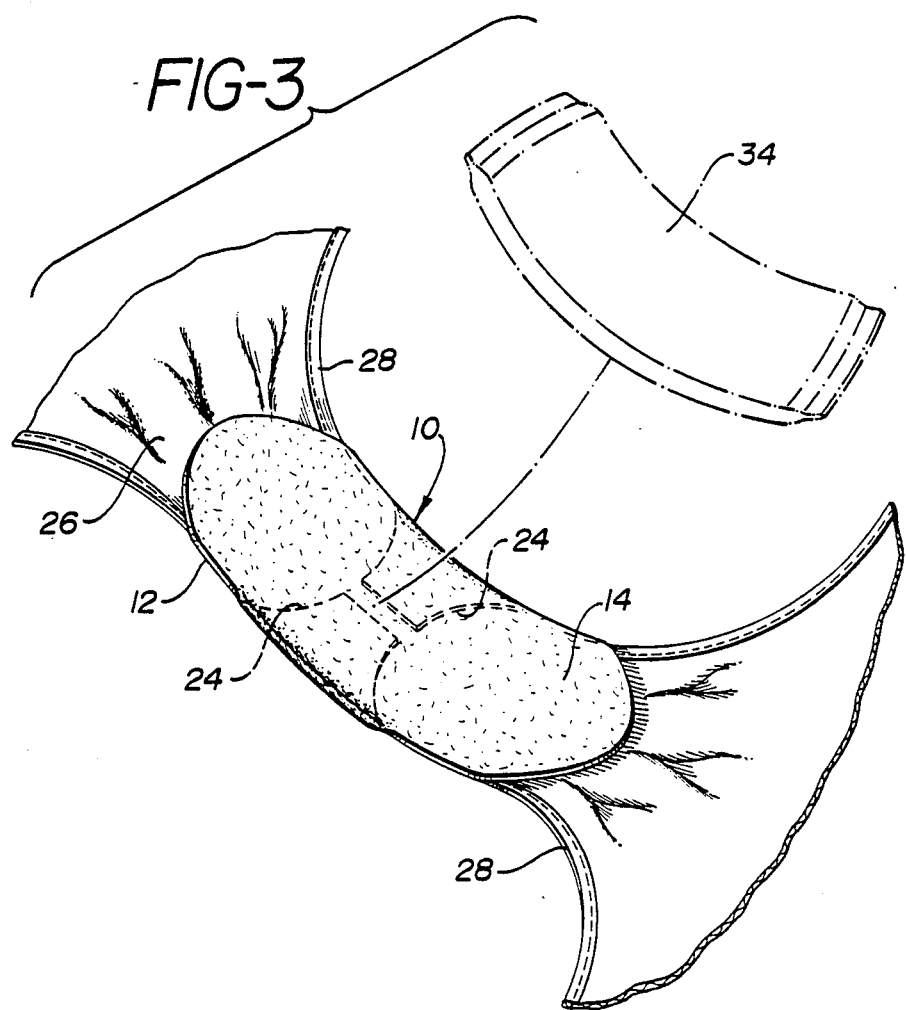

PANTY PROTECTOR

This is a continuation of application Ser. No. 018,259, filed Feb. 24, 1987.

BACKGROUND OF THE INVENTION

This invention relates to products designed to be worn in the inner crotch portion of an undergarment to protect the undergarment from soiling and, in particular, this invention relates to such a product for use alone or in conjunction with other sanitary napkins or panty shields to protect the undergarment from body fluids either inter or intra-menstrually.

A great number of products and suggestions exist directed to products designed to protect undergarments from soiling due to discharge of body fluid. Almost invariably, such products comprise a body fluid impervious barrier, generally on the garment facing side of the product, to prevent transmission of fluid through the product into the garment. Additionally, such product usually employ one or more layers of body fluid absorbent material, on the body facing side of the impervious barrier, to absorb and retain body fluid discharge and prevent such discharge from flowing over or around the barrier and onto the garment. Several of such prior products are also provided with pressure sensitive adhesive means disposed on the garment side of the products and provided for adhering the product to the inner crotch portion of the undergarment. An example of such product is described in U.S. Pat. No. 3,315,677 issued to Tyrrell, Jr. on Apr. 25, 1967.

Additionally, it has been suggested that the generally longitudinally extending products be enhanced by the addition of transversely extending wings or flaps to provide further protection against undergarment soiling and a more secure attachment system. Examples of such suggestions may be found in U.S. Pat. No. 2,787,271, issued to Clark on Apr. 2, 1957; U.S. Pat. No. 3,397,697, issued to Rickard on Aug. 20, 1968; U.S. Pat. No. 4,285,343, issued to McNair on Aug. 25, 1981; and U.S. Pat. No. 4,589,876, issued to Van Tilbury on May 20, 1986.

Referring, for example, to the McNair or the Rickard patents, the flaps are provided with adhesive means and, when the central portion of the product is implaced into the inner crotch portion, the flaps are employed to encircle the crotch portion and be secured about the outer surface of the crotch portion by use of such adhesive means.

To a degree, the complexity of the design of the above described flapped panty protectors is at war with the concept of an inexpensively produced product, capable of being sold at a price low enough for the consumer to purchase and use only once and then dispose of. While the flaps certainly add to the amount of material going into a product, more importantly the addition of flaps integral with the product greatly increase the so-called "waste material" which is discarded during the manufacture of the product. Thus, for example, if one was to manufacture such products as taught in the Rickard, McNair or Van Tilburg patents with integral flaps, it would be most desirable to cut such products from sheet material or sheet-like laminates of the various layers. Unfortunately, if one attempted to do this, because of the shape of the periphery of the product, a great quantity of such sheet material would be wasted.

It can be seen that the complications in designs of the so-called flapped panty protectors have concommittently increased the difficulty in mass producing such products commercially. Accordingly, there is a need for a product which incorporates the desirable features of the flapped napkins of prior suggestions but which is capable of being inexpensively manufactured and, of course, there is a need for a process for the manufacture of such products.

SUMMARY OF THE INVENTION

In accordance with the teachings of this invention a panty protector is provided, together with a process of making the same, which protector is capable of being mass produced, inexpensively, with minimal material waste.

Specifically, improvements are made in a panty protector of the kind for adhesive attachment to the crotch portion of an undergarment. Such protector comprises a generally longitudinally extending central portion and is provided with transversely extending flaps. The panty protector has a longitudinal center line, a transverse center line and a periphery defined by a closed curve. The closed curve is of such a shape that a portion of the periphery of each of a plurality of identically shaped protectors may be butted against a portion of the periphery of the protector so as to completely and continuously circumscribe the periphery while leaving no space between abutting protectors and having no part of any protector overlie another. By so selecting such a shape for the closed curve of the periphery of the protector, it is now possible to produce a sheet or laminate of the material of construction for the protector and then simply cut such shapes out of said sheet with minimum waste.

In an embodiment of this invention the periphery of the protector may be defined as being oriented by reference to a planar Cartesian coordinate system wherein the longitudinal center line, Y—Y, is the ordinate, the transverse center line, X—X, is the abscissa; and, of course, the intersection of the abscissa and the ordinate is the origin o. Accordingly, curve segments of the closed curve constituting the periphery of the product will lie in each of the four quadrants defined by such coordinate system. In accordance with the teachings of this invention, the curve segment found in a first of such quadrants must be congruent and unidirectional with the curve segment lying in the quadrant diagonally opposite to said first quadrant. By the term "congruent" and "unidirectional" it is meant the each point on the curve sequent having a position $(X_i, Y_i)$, as defined by the described coordinate system, has a corresponding part in the diagonally opposite quadrant having a location $(-W+X_i)$, $(-L+Y_i)$ wherein W is one half the width of the protector at its widest point and L is the sum of onehalf the length of the protector at its longest point plus one half the length of the extreme lateral edge of the flaps.

When a protector is so designed, essentially no waste is generated in the course of manufacture. Additionally, it is possible to apply attachment means to such a product in a more efficient manner.

BRIEF DESCRIPTION OF THE DRAWINGS

FIG. 1 is a perspective view of a panty protector embodying the teachings of this invention;

FIG. 2 is a transverse cross-sectional view of the protector of FIG. 1, taken through line 2—2;

FIG. 3 is a schematic view of the protector of FIG. 1, placed into the inside crotch portion of a panty and of a sanitary napkin to be placed thereupon;

DETAILED DESCRIPTION OF THE INVENTION

Figure 4:
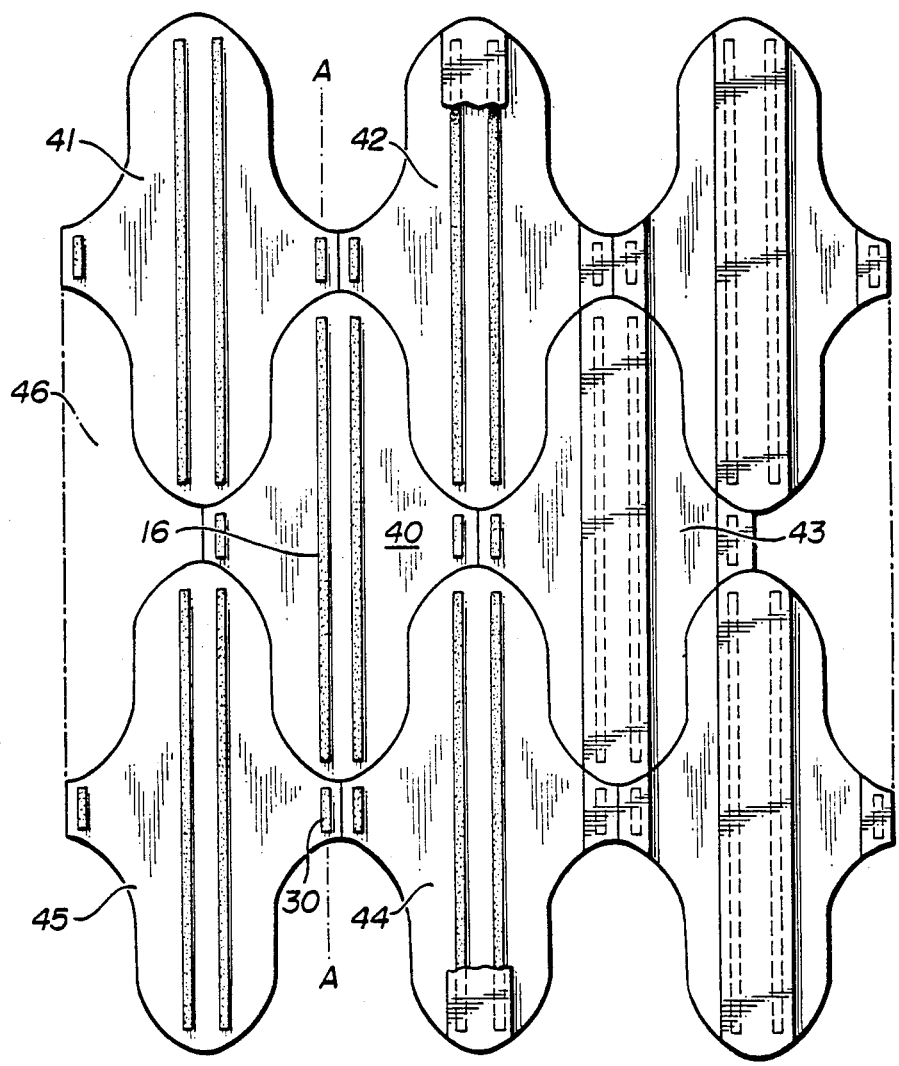
FIG. 4 is a plurality of panty protectors as they might be produced from a single laminate sheet.

Referring now to the drawings, illustrated in FIGS. 1 and 2 is a panty protector 10 embodying the teachings of this invention. The protector 10 has a garment facing side 12 to be placed against the inside crotch portion of an undergarment and a body facing side 14 worn facing toward the body. The protector 10 may be provided with means for affixing the protector to the inside crotch portion of the undergarment such as, for example, pressure sensitive adhesive means 16. Such means are illustrated, in this embodiment, as two longitudinally extending lines. The pressure sensitive adhesive may be any of the well known compositions suitable for this purpose including, for example, the water based pressure sensitive adhesives such as the acrylate adhesives, e.g. vinyl acetate-2 ethyl hexyl acrylate copolymer which are generally combined with tackefiers such as for example, ethylene amine. Alternatively, the adhesive may comprise the rapid setting thermoplastic (hot melt) adhesives such as block copolymers exemplified by styrene and butadiene/styrene copolymers. The adhesive elements may also comprise a two-sided adhesive tape.

The adhesive elements are protected by a release strip 18 to avoid undesirable adhesion prior to use and are shown in FIG. 1 partially peeled from the adhesive elements 16. The release strip 18 may be made of any suitable sheet-like material which adheres with sufficient tenacity to the adhesive elements 16 to remain in place, but which can be readily removed when the protector 10 is to be used. A particularly useful material is a semi-bleached kraft paper, the adhesive contacting side of which has been silicone coated to provide easy removal from the adhesive just prior to use.

As can be best viewed in FIG. 2, the protector of the illustrated embodiment comprises a sheet like laminate of two layers: a garment facing barrier layer 20 and a body facing cover layer 22. It will be understood that while such laminate structure is desirable, it is possible that the protector may be needed only for an absorbent function or a comfort function in which case the barrier layer 20 may be dispensed with. On the other hand, the protector may be needed only for a protective function and the cover layer 2 may be dispensed with. It is also possible that in additionn to these two layers, further layers serving the same or other functions may be employed.

For the illustrated embodiment, the barrier layer 20 is provided to preclude body fluid from passing onto an undergarment and may be constructed of any material suitable for this purpose. For example, layer 20 may be a polymeric film such as polyethylene or polypropylene or may be a normally fluid pervious that has been treated to be impervious such as a fluid repellent paper. Polyethylene film having thickness of from one half to five mils is the material of choice.

The cover layer 22 may be any material which is either soft or absorbent or both and is preferably a non-woven fabric such as these used as body facing covers in sanitary napkin or as absorbents in body fluid absorbing products. A material of choice is a mixture of rayon fibers and heat bondable polyester/polyethylene conjugate fibers. Such conjugate fibers are fibers which comprise a polyester core surrounded by a sheath of polyethylene. Preferably, the conjugate fibers employ high density polyethylene, that is, linear polyethylene that has a density of at least 0.94 gm/cc and a Melt Index (as determined by ASTM D-1288E method, employing the parameters of 190° C. and 2160 gms.) of greater than 1, preferably greater than about 10, and more preferably from about 20 to about 50. The fibers may comprise from about 40 to about 60 percent, by weight of polyester and, preferably from about 45 to about 55 percent, by weight of polyester, with the remainder being polyethylene. Such fibers may be used in deniers of from about 1 to about 6 and may be from about ½ inch (1.27 cm) to about 3 to 4 inches (7.62 to 10.16 cm) long.

These conjugate fibers are combined with rayon fibers in a conjugated fiber to rayon ratio of from about 50/50 to about 10/90, and, for example, 20/80. The rayon employed may have a denier ranging from about 1.5 to 6.0, such as 3.0 and a staple length of from about 0.25 in. to 2.0 in., such as 1.5 in. The non-woven fiber may be stabilized by applying heat thereto, preferably at low or even essentially zero pressure to obtain thermal bonding without destroying the integrity of the fibers. The fabric may be utilized in basis weights of from about 0.75 to 3.0 oz./yd$^2$, such as for example 1.0 oz./yd$^2$.

In accordance with this invention, the protector is provided with integral flaps for protecting the undergarment. As illustrated in FIG. 3, the protector is emplaced into the inner crotch portion of an undergarment 26 and adhered thereto using the adhesive element 16. The flaps 24 are then encircled about the longitudinal edges 28 of the crotch portion of the undergarment to overlie the exterior crotch portion. The flaps are adhered in place by use of adhesive areas 30 (see FIGS. 1 and 2) which areas may be protected prior to use with release strips 32. Thus it can be seen that the undergarment is protected not only on its inside crotch surface but also at its longitude edges and the protector is securely in place. A sanitary napkin 34 may be used in conjunction with protector 10.

As described herein it is a feature of this invention to design a protector which can be manufactured with minimum waste and preferably one which can be cut from a single sheet of laminated material with minimum waste. Accordingly, the shape of the periphery of the protector is specifically chosen to enable such objectives to be realized. Referring to FIG. 4, illustrated therein is plurality of protectors each having a shape which allows them to be cut from a single sheet with minimum waste. In examining FIG. 4, it can be seen that the peripheral shape of the identically shaped protectors is choosen such that a portion of the periphery of each of a plurality of identically shaped protectors, e.g., protectors 41, 42, 43, 44, 45 and 46 may be butted against a portion of the periphery of the protector 40 so as to completely and continuously circumscribe the periphery of protector 40 while leaving no space between abutting protectors and having no part of any protector overlie another.

Figure 5:
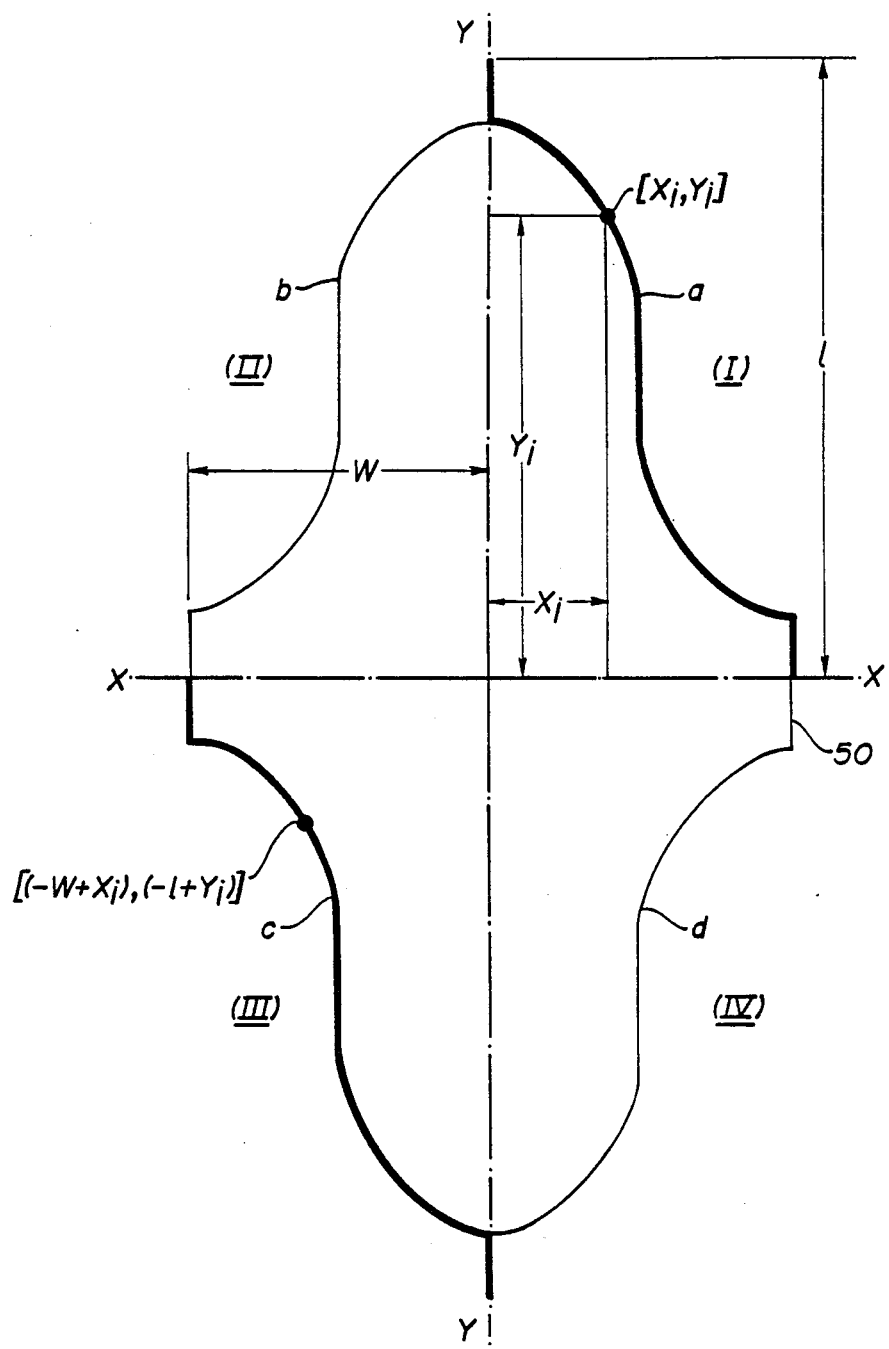
FIG. 5 is a schematic plan top view of the protector of FIG. 1 further illustrating the peripheral shape thereof.

The desired relationships of the curve portions forming the periphery of the protector and satisfying the above requirements are best illustrated in FIG. 5

(wherein the use of the conventionally shown heavy shade lines are omitted for the purpose of clarity). As is illustrated the periphery of the protector is defined as being oriented by reference to a planar Cartesian co-ordinate system wherein the longitudinal centerline of the protector, line Y—Y, is the ordinate; the transverse centerline, line X—X, is the abscissa; and, of course, the intersection of the abscissa and the ordinate is the origin. Accordingly, curve segments (a, b, c, and d) of the closed curve constituting the periphery of the protector each lie in each of the four quadrants (I, II, III and IV, respectively) defined by the co-ordinate system.

In accordance with the teachings of this invention, the curve segment found in a first of such quadrants, e.g., curve segment a, in quadrant I, must be congruent and unidirectional with the curve segment lying in the diaginally opposite quadrant, i.e., curve segment c, in quadrant III. Stated in terms of the Cartesian co-ordinate system, for each point on curve segment a, e.g., the point having a position $[X_i, Y_i]$, there is a corresponding point on curve segment c having a position $[(-W+X_i), (-1+Y_i)]$ wherein:

W is one half the width of the protector at its widest part; and 1 is the sum of one-half the length of the protector at its longest point plus half the width of the extreme lateral edge 50 of the flap.

It should be noted that, by adhering to the teachings of this invention, in addition to the substantial savings in waste material, several other processing advantages accrue. Referring again to FIG. 4, it can be seen that a single sheet of material or laminate may be employed and cut with minimum waste into the protectors of this invention. It should also be noted that the adhesive elements of the product may be alligned in one direction, e.g., the machine direction, for a line producing the product. For example, adhesive laid down along line A—A passing through protector 40 may be applied by a nozzle timed to produce a first short line, corresponding to adhesive area 30, spaced apart from and alternating with a long line corresponding to adhesive element 16. It can be seen then that all the adhesive for each of the protectors may be aplied by properly spaced and timed nozzles.

Simmilarly, the protector strips 18 and 32 may be applied from a row of strip applicators in parallel continuous rows. Thereafter, having applied the adhesive and the protective strips, the sheet may be cut into individual protectors.

I claim:

1. A method for manufacturing panty protectors for adhesive attachment to the crotch portion of an undergarment comprising a generally longitudinally extending central portion and transversely extending flaps; said panty protectors each having a longitudinal center line and a transverse center line and having a closed curve defining the outer periphery of each protector, comprising:

(a) cutting a plurality of protectors from a sheet of material, such that the protectors are identically shaped in a portion of the periphery of each protector is butted against a portion of the periphery of each adjacent protector so as to substantially continuously circumscribe the periphery of each protector, leaving substantially no space between abutting protectors and no part of any protector overlies another protector in such that all protectors are oriented in the same direction along an axis of the sheet of material; and, (b) applying adhesive in at least two, spaced apart, longitudinally extending centrally located adhesive elements with said flaps being provided with at least one longitudinally extending adhesive element spaced from the extreme lateral edges of said flaps, and wherein the space between the central adhesive elements is twice the space between the adhesive elements on the flaps in said lateral edge; such that said adhesive lines are applied alternately in the longitudinal direction to the flaps of a first panty protector and then to the central absorbent portion of a second panty protector.

* * * * *